(12) United States Patent
Feugnet et al.

(10) Patent No.: US 10,077,218 B2
(45) Date of Patent: Sep. 18, 2018

(54) PROCESS FOR CONVERTING A HEAVY FEED INTO MIDDLE DISTILLATE

(75) Inventors: Frederic Feugnet, Lyons (FR); Francois Hugues, Vernaison (FR); Mai Phuong Do, Courbevoie (FR); Romain Roux, Rueil Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 1069 days.

(21) Appl. No.: 13/989,590

(22) PCT Filed: Nov. 3, 2011

(86) PCT No.: PCT/FR2011/000589
§ 371 (c)(1),
(2), (4) Date: Jul. 15, 2013

(87) PCT Pub. No.: WO2012/069709
PCT Pub. Date: May 31, 2012

(65) Prior Publication Data
US 2013/0281749 A1      Oct. 24, 2013

(30) Foreign Application Priority Data

Nov. 25, 2010 (FR) ..................... 10 04585

(51) Int. Cl.
*C07C 2/06* (2006.01)
*C10G 11/18* (2006.01)
(Continued)

(52) U.S. Cl.
CPC ............... *C07C 2/06* (2013.01); *C10G 11/18* (2013.01); *C10G 50/00* (2013.01); *C10G 57/02* (2013.01);
(Continued)

(58) Field of Classification Search
CPC ........... C07C 2/06; C07C 9/16; C07C 15/107; C07C 9/14; C07C 5/2791;
(Continued)

(56) References Cited

U.S. PATENT DOCUMENTS 3,954,600 A      5/1976 Gladrow et al.
4,720,600 A *    1/1988 Beech et al. ................. 585/330
(Continued)

FOREIGN PATENT DOCUMENTS

EP      0392590 A1     10/1990
FR      2659346 A1      9/1991
WO    2010/117539 A2   10/2010

OTHER PUBLICATIONS

Melpolder, F.W.; Brown, R.A.; Young, W.S.; Headington, C.E. "Composition of Naphtha from Fluid Catalytic Cracking", Ind. Eng. Chem., (1952), pp. 1142-1146.*
(Continued)

*Primary Examiner* — Philip Y Louie
*Assistant Examiner* — Aaron W Pierpont
(74) *Attorney, Agent, or Firm* — Millen White Zelano and Branigan, PC; John Sopp

(57) ABSTRACT

The present invention describes a process for the conversion of a heavy feed which can be used to improve the selectivity for middle distillate. The process employs a catalytic cracking unit followed by one or more units for the oligomerization of C2 to C9 olefins which can preferentially produce an additional cut termed the middle distillate. The light portion of the oligomerate produced which cannot be incorporated into the middle distillate cut is recycled to the FCC unit for cracking into light olefins which are returned to the oligomerization units as a supplement to the olefins of the feed in order to preferentially form heavy oligomerates which can be incorporated into the middle distillate cut.

12 Claims, 1 Drawing Sheet

(51) Int. Cl.
*C10G 50/00* (2006.01)
*C10G 57/02* (2006.01)

(52) U.S. Cl.
CPC .................. *C10G 2300/301* (2013.01); *C10G 2300/4006* (2013.01); *C10G 2300/4012* (2013.01); *C10G 2400/04* (2013.01); *C10G 2400/06* (2013.01); *C10G 2400/08* (2013.01)

(58) Field of Classification Search
CPC ............ C10G 2300/4012; C10G 11/18; C10G 57/02; C10G 2400/06; C10G 50/00; C10G 2400/04; C10G 2300/4006; C10G 2300/301; C10G 2400/08; C10L 1/06
USPC ........................................................ 585/315
See application file for complete search history.

(56) References Cited

U.S. PATENT DOCUMENTS

| | | | |
|---|---|---|---|
| 4,822,477 A | 4/1989 | Avidan et al. | |
| 4,966,680 A | 10/1990 | Avidan et al. | |
| 5,846,403 A * | 12/1998 | Swan ..................... | C10G 11/18 208/113 |
| 5,981,818 A | 11/1999 | Purvis et al. | |
| 6,027,707 A * | 2/2000 | Casci et al. .................. | 423/705 |
| 2001/0032802 A1* | 10/2001 | Mon ..................... | C10G 11/18 208/74 |
| 2006/0178546 A1* | 8/2006 | Mo et al. ...................... | 585/648 |
| 2006/0191820 A1* | 8/2006 | Mo ........................ | C10G 11/05 208/120.1 |
| 2009/0030251 A1* | 1/2009 | Senetar ................ | C10G 57/005 585/324 |

OTHER PUBLICATIONS

International Search Report for PCT/FR2011/000589 (dated Oct. 24, 2012).

* cited by examiner

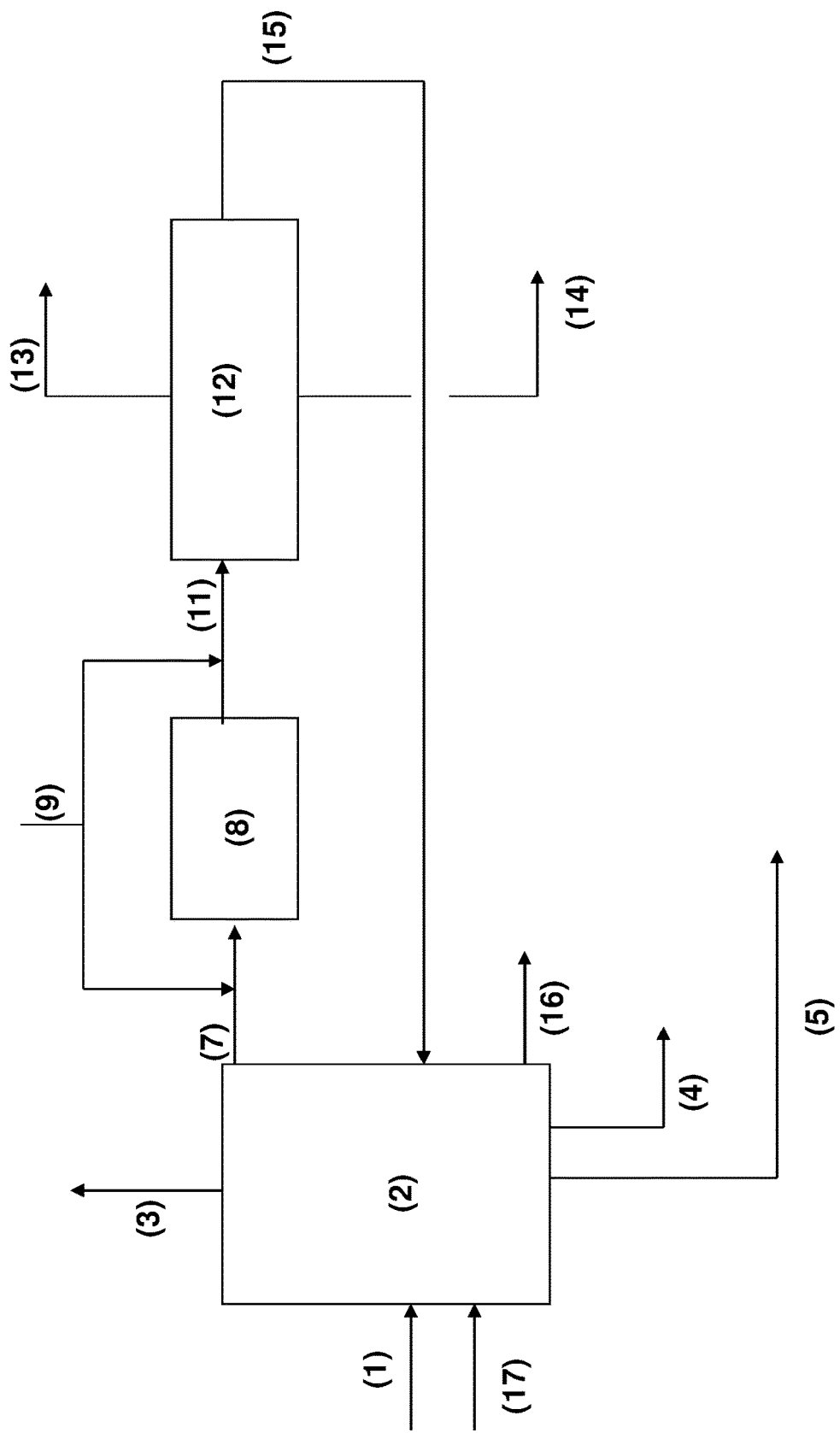

PROCESS FOR CONVERTING A HEAVY FEED INTO MIDDLE DISTILLATE

FIELD OF THE INVENTION

The invention relates to a process for the conversion of a heavy hydrocarbon feed having improved selectivity for middle distillate. More precisely, the process of the present invention can be used to co-produce gasoline with a reduced yield and to improve middle distillate production by at least 2% by weight with respect to the feed, an increment which is highly significant in view of the tonnages involved in the process.

Historically, catalytic cracking units, known by the abbreviation FCC for "fluid catalytic cracking", are optimized for the production of light products: liquefied gases (or LPG), light olefins, and gasoline, in order to satisfy the demands of the polymers market which requires the polymerization of light olefins, and consumption requirements of the automotive vehicle market for gasoline.

In that type of function, the production of gas oil bases remains limited. Until now, given that the automotive vehicle market is turning more and more to diesel, the demand for gas oil type products has been greatly increased. As a consequence, it is becoming increasingly necessary to orientate refinery production towards the production of gas oil bases and to limit the production of gasoline.

FCC units, which are present in practically half of refineries, are both the principal source of gasoline and a major source of light olefins; thus, it is vital to be able to convert such units into units promoting the production of gas oils.

The present invention describes a solution which can both improve the production of gas oil bases in fluid catalytic cracking units (FCC) and limit the production of gasoline.

The present invention essentially consists of a concatenation of a FCC unit with one or more oligomerization units orientated towards the production of middle distillate, a concatenation which employs a specific recycle which can significantly improve the middle distillate yield, but also the selectivity of that cut compared with the gasoline, thereby accomplishing the aim of reducing gasoline production.

In the prior art, the FCC process can convert heavy hydrocarbon feeds with an initial boiling point which is generally over 340° C. into lighter hydrocarbon fractions, in particular a gasoline cut, by cracking molecules of the heavy feed in the presence of an acid catalyst.

Again in the prior art, FCC also produces liquefied petroleum gas (LPG) in large quantities with high olefins contents.

The process of the present invention may generally be presented as a process for the production of middle distillate with a reduction in the gasoline cut.

The present invention employs a catalytic cracking unit followed by one or more units for the oligomerization of C2 to C9 olefins, in the knowledge that this may be formed by several disjointed cuts such as, for example, a C3 to C6 cut and a C8 to C9 cut, in order to preferentially produce an additional middle distillate cut. For simplicity, in the remainder of the text, we shall refer to a wide cut to designate the series of distinct cuts containing 2 to 9 carbon atoms.

The invention essentially resides in the concatenation of these two processes as well as in recycling the light portion of the oligomerate produced (which cannot be incorporated into the middle distillate cut) to the FCC riser for re-cracking therein into light olefins which are returned to the oligomerization units as a supplement to the olefins of the feed in order to preferentially form heavy oligomerates which can be incorporated into said middle distillate cut.

This specific recycle can very significantly improve the middle distillate selectivity of the process. The reduction in the gasoline cut yield results on the one hand from the production of middle distillate by the oligomerization of C2 to C9 olefins and on the other by the cracking of the light oligomerates in the FCC with a view to the production of light olefins which are themselves returned to one or more of the oligomerization units.

This set of characteristics defines a process with substantially improved selectivity for middle distillate.

The present invention is compatible with all catalytic cracking reactor technologies, whether it be a riser or a downer mode technology.

The catalytic cracking unit employed in the present process can be broken down into several modes, using a single or several reactors, each reactor being able to function in riser or downer mode.

If several oligomerization units are associated with a catalytic cracking unit, they may be arranged in series or in parallel.

EXAMINATION OF THE PRIOR ART

Patent application FR 2 935 377 concerns a process for the conversion of a hydrocarbon feed termed a heavy feed with a view to the co-production of propylene and gasoline in a minimum yield. The process of that invention comprises at least two reaction steps, a first, catalytic cracking step and a second step for the oligomerization of C3 and C4 olefins or C4 olefins or C4 and C5 olefins from the catalytic cracking step. A third reaction step for the selective hydrogenation of olefins may be necessary in certain cases before the oligomerization step.

The process of the present invention can carry out two types of production corresponding to two distinct working scenarios:
a "maxi propylene" scenario, corresponding to maximum production of propylene while keeping the gasoline yield at a minimum, or even slightly increased compared to the potential yield from the catalytic cracking unit alone; or
a "maxi gasoline" scenario, corresponding to maximum production of gasoline without the production of propylene.

Patent WO 03/078547 describes a process for the catalytic cracking of a principal feed with a boiling point of more than 350° C. and a relatively light secondary feed with a boiling point of less than 320° C., said secondary feed being constituted by olefins containing at least 8 carbon atoms produced by oligomerization of light olefins containing 4 or 5 carbon atoms.

Patent WO 03/078364 describes a process for the production of oligomers from C4 olefins, said oligomers subsequently being cracked in a catalytic cracking unit with a view to maximizing the production of propylene.

One essential difference of the present invention over the prior art processes cited above lies in recycling the light portion of the oligomerate produced by the oligomerization unit; this portion cannot be incorporated into the middle distillate cut. This light portion of the oligomerate is re-cracked in the riser of the FCC unit into light olefins which are returned to the oligomerization unit as a supplement to the olefins of the feed, in order to preferentially form heavy oligomerates which can be incorporated into the middle distillate cut.

As a result, this specific recycle, which has not been described in the prior art, can very significantly improve the selectivity for middle distillate of the process.

The reduction of the gasoline cut yield appears to be a result of the production of middle distillate on the one hand by the oligomerization of olefins included in the wide C2 to C9 cut (in the knowledge that this may be formed by several disjointed cuts such as a C3 to C6 cut and a C8 to C9 cut), and on the other hand by cracking the light oligomerates in the FCC.

BRIEF DESCRIPTION OF THE FIGURE

The FIGURE represents a layout for the process of the invention which shows the FCC unit 2, the oligomerization unit or units 12 and the optional hydrotreatment unit or units 8.

BRIEF DESCRIPTION OF THE INVENTION

The invention concerns a process for the conversion of a hydrocarbon feed known as a heavy feed, i.e. constituted by hydrocarbons with a boiling point of more than approximately 340° C., with a view to improving the production of middle distillate and of reducing the production of gasoline.

The process of the invention comprises at least two reaction steps, a first catalytic cracking step 2 and a second step for the oligomerization of olefins 12 included in a wide C2 to C9 range cut.

The term "wide C2 to C9 range cut" means a cut that is primarily constituted by olefins, said cut possibly being formed from several disjointed cuts such as a C3 to C6 cut and a C8 to C9 cut, for example, derived from catalytic cracking, or any other cut that is rich in C2 to C9 olefins derived from other units, such as a coking unit, visbreaking unit, MTO (methanol to olefins conversion) unit or any other process for the transformation of alcohol into olefins, a steam cracking unit or a Fischer-Tropsch synthesis unit, used alone or as a mixture.

The term "primarily" means at least 80% by weight, preferably at least 90% by weight of olefins.

A description of coking, visbreaking and steam cracking units can be found in the reference work "Raffinage et génie chimique" [Refining and chemical engineering] by P Wuithier, published by Technip.

The process of the invention accomplishes two aims:
an improvement in the production of middle distillate;
a reduction in the production of gasoline.

The middle distillate cut corresponds to a hydrocarbon cut with a distillation range in the range 130° C. to 410° C., preferably in the range 150° C. to 390° C.

The primary aim of improving the middle distillate production is achieved as follows:
by sending the olefins of the wide C2 to C9 cut produced by catalytic cracking, 7, to one or more oligomerization units 12 operated under specific operating conditions in order to produce a middle distillate;
by recycling to the riser of the FCC unit 2 the light portion of the oligomerate produced by the oligomerization process which corresponds to olefins with a boiling point of less than 180° C. and preferably less than 150° C. This light cut, which cannot be incorporated into the middle distillate cut, may thus be re-cracked in the FCC unit 2 into light olefins which are returned to the oligomerization units 12 as a supplement to the olefins of the feed in order to preferentially form heavy oligomerates 14 with a boiling point of more than 130° C., preferentially more than 150° C.

These heavy oligomerates 14 can be incorporated into the middle distillate cut.

It is also possible in the present invention to recycle to the catalytic cracking unit 2 any cut which is rich in C2 to C9 olefins which may be formed from several disjointed cuts such as, for example, a C3 to C6 cut and a C8 to C9 cut derived from other units such as, for example, the coking unit, visbreaking unit, the MTO (methanol to olefins conversion) unit, or from any other process for the transformation of alcohol into olefins, steam cracking or Fischer-Tropsch synthesis, used either alone or as a mixture. These olefins deriving from an external unit are represented in the FIGURE by the stream 17.

The second aim, namely reduction of gasoline production, is achieved as follows:
by a recycle of the light oligomerate fraction 15 to the FCC riser in order to be converted into light olefins; in the prior art, that oligomerate fraction would have been incorporated into the gasoline cut.

The heavy feed 1 is cracked in a fluid catalytic cracking reactor in the presence of a cracking catalyst.

The light fraction 15 of the oligomerate derived from the oligomerization of C2 to C9 olefins, 12, is cracked with the same cracking catalyst, separately or as a mixture with the heavy feed 1. This second feed, termed the secondary feed 15, has a boiling point which is preferably below 180° C., preferably less than 150° C. A third feed 17 of C2-C9 olefins deriving from units outside the present process may be cracked as a mixture with the secondary feed 15.

The effluents from catalytic cracking 2 are sent to a fractionation zone and the catalyst used for catalytic cracking is regenerated in a regeneration zone. When the catalytic cracking unit is composed of several risers or possibly downers, said catalyst regeneration zone is a common zone.

The olefin-rich cut 7, principally constituted by olefins containing 2 to 9 carbon atoms derived from catalytic cracking 2, is sent in part or in its entirety to one or more oligomerization units 12. A pre-treatment 8 to remove impurities such as nitrogen-containing compounds or diolefins may be necessary upstream of the oligomerization unit. Similarly, it is possible to modify all or a portion of the olefin-rich cut 7 by means of olefin-converting processes, for example etherification, alkylation, or partial oligomerization, before being sent to the oligomerization unit 12.

This is then termed partial oligomerization, to distinguish it from the principal oligomerization 12 forming an integral part of the process of the invention.

The oligomerates formed are separated by distillation into a cut termed a light oligomerate 15 and a cut termed a heavy oligomerate 14. The light oligomerate cut 15 has a boiling point of less than 180° C., preferably less than 150° C.

Said light oligomerate cut 15 constitutes the secondary feed which is recycled to the FCC reaction zone 2. The heavy oligomerate cut 14 has a boiling point of more than 130° C., preferably more than 150° C., and is incorporated into the middle distillate.

As will be disclosed in the next paragraph, the catalytic cracking unit 2 can be broken down into several modes with a single reactor treating the heavy feed 1 and the recycle of the light oligomerate 15 and the olefins 17 deriving from the outside units, or two reactors, one treating the heavy feed 1 and the other treating the light feeds 15 and 17.

Further, each reactor may function in riser or downer mode.

When several oligomerization units 12 are associated with the catalytic cracking unit 2, they may be arranged in series or in parallel.

DETAILED DESCRIPTION OF THE INVENTION

According to the invention, the overall feed to be cracked contains more than 50% by weight of hydrocarbons with a boiling point of more than 340° C. In general, the feed 1 is constituted by a vacuum distillate, or possibly an atmospheric residue. The overall cracked feed may contain up to 100% by weight of hydrocarbons with a boiling point of more than 340° C.

The secondary feed 15, termed the light oligomerate, deriving from the oligomerization unit 12, generally contains 2% to 40% by weight, usually 4% to 30% by weight, and preferably 6% to 25% by weight of an olefin-rich cut principally constituted by olefins containing 2 to 9 carbon atoms, said olefin-rich cut possibly being formed from a plurality of disjointed cuts such as, for example, a C3 to C6 cut and a C8 to C9 cut having been produced by oligomerization of olefins containing 2 to 9 carbon atoms.

The secondary feed 15 may also comprise other oligomerates 17 essentially formed from C2 to C9 olefins, as well as any C2 to C9 olefin-rich cut derived, for example, from a coking unit, a visbreaking unit, a MTO (methanol to olefin conversion) unit or any other process for transforming alcohol to olefins, and a steam cracking unit.

In accordance with the invention, the cracking catalyst is constituted by a matrix of alumina, silica or silica-alumina with or without an ultra-stable Y type zeolite dispersed in that same matrix. Adding an additive based on ZSM-5 zeolite, with the quantity of ZSM-5 crystals in the total quantity in the cracking unit being less than 30% by weight, may also be envisaged.

The invention may thus be defined as a process which can improve the production of the middle distillate cut and reduce the production of the gasoline cut starting from a heavy hydrocarbon feed 1 with an initial boiling point of 340° C. or more, said process employing a catalytic cracking unit 2 followed by one or more oligomerization units 12 functioning in middle distillate mode, in which process the feed for the oligomerization unit (7 becoming 11 after optional hydrotreatment) is constituted by a cut containing 2 to 9 carbon atoms which may be formed from several disjointed cuts, such as, for example, a C3 to C6 cut and a C8 to C9 cut derived from the FCC unit.

The effluents from the oligomerization unit 12 are separated by distillation or any other means into three cuts:
- a cut 13, termed the raffinate, which corresponds to unconverted olefins and to paraffins of the feed 11;
- a cut termed a light oligomerate, 15;
- and a cut termed a heavy oligomerate, 14.

The light oligomerate cut 15 has a boiling point of less than 180° C., preferably 150° C. This cut constitutes the secondary feed which is recycled to the riser of the FCC. The cut termed the light oligomerate 15 may also be supplemented with any C2 to C9 olefin-rich cut 17 possibly being formed from several disjointed cuts, such as a C3 to C6 cut and a C8 to C9 cut, for example, with a boiling point of less than 180° C., preferably less than 150° C., derived from other processes such as, for example, the coking process, the visbreaking process, the MTO process (or any other process for transforming alcohol to olefins), the steam cracking process or the Fischer-Tropsch synthesis process, said cuts 17 possibly being recycled alone or as a mixture. Said various light oligomerate cuts derived from units other than the oligomerization units 12 are represented by the stream 17.

The heavy oligomerate cut 14 has a boiling point of more than 130° C., preferably more than 150° C. Said cut, termed the heavy oligomerate, is incorporated into the middle distillate produced by the catalytic cracking unit.

The catalytic cracking unit 2 may comprise a single reactor treating both the heavy feed and the secondary feed, or two distinct reactors with one treating the heavy feed 1 and the other treating the light feed 15+17. In addition, each of the reactors may be a riser or a downer. Usually, the two reactors will have the same mode of flow.

When catalytic cracking is carried out in a single riser reactor, the reactor outlet temperature (ROT) is in the range 450° C. to 650° C., preferably in the range 470° C. to 620° C., and the ratio C/O is in the range 2 to 20, preferably in the range 4 to 15.

When the reactor is a downer, the reactor outlet temperature (ROT) is in the range 480° C. to 650° C., and the C/O ratio is in the range 10 to 50.

When catalytic cracking is carried out in two distinct riser FCC reactors, the first FCC reactor carrying out cracking of the heavy feed 1 operates at a reactor outlet temperature (ROT1) in the range 450° C. to 650° C., preferably in the range 470° C. to 620° C., and a C/O ratio in the range 2 to 20, preferably in the range 4 to 15. The second FCC reactor, carrying out cracking of the light oligomerate cut derived from the oligomerization unit 15 or from external units 17, operates at a reactor outlet temperature (ROT2) in the range 500° C. to 750° C., preferably in the range 570° C. to 650° C., with a ratio C/O in the range 8 to 40.

When catalytic cracking is carried out in two distinct FCC reactors in downer mode, the first FCC reactor carrying out cracking of the heavy feed operates at a reactor outlet temperature (ROT1) in the range 480° C. to 650° C. with a C/O ratio in the range 10 to 50, and the second FCC reactor, carrying out cracking of the light oligomerate cut derived from the oligomerization unit 15 or from external units 17, operates at a reactor outlet temperature (ROT2) in the range 570° C. to 750° C., with a ratio C/O in the range 10 to 50.

The streams of spent catalyst from the two FCC reactors are separated from the cracking effluents by any system for separating gas from solid known to the skilled person, and regenerated in a common regeneration zone.

The particular conditions for the various units of the process of the invention are described below in more detail.
1) Catalytic Cracking (FCC):

The catalyst for the FCC reactor is typically constituted by particles with a mean diameter generally in the range 40 to 140 micrometers (1 micron=$10^{-6}$ meter), and usually in the range 50 to 120 micrometers.

The catalytic cracking catalyst contains at least one appropriate matrix such as alumina, silica or silica-alumina, with or without the presence of a Y type zeolite dispersed in said matrix.

The catalyst may also comprise at least one zeolite with form selectivity selected from one of the following structure types: MEL (for example ZSM-11), MFI (for example ZSM-5), NES, EUO, FER, CHA (for example SAPO-34), MFS, MWW. It may also comprise one of the following zeolites: NU-85, NU-86, NU-88 or IM-5, which also have form selectivity.

The advantage of said zeolites with form selectivity is that better propylene/isobutene selectivity is the result, i.e. a propylene/isobutene ratio which is higher in the cracking effluents.

The proportion of zeolite with form selectivity compared with the total quantity of zeolite may vary as a function of the feeds used and of the structure of the desired products. Frequently, 0.1% to 60%, preferably 0.1% to 40%, and in particular 0.1% to 30% by weight of zeolite with form selectivity is used.

The zeolite or zeolites may be dispersed in a matrix based on silica, alumina or silica-alumina, the proportion of zeolite (all zeolites together) with respect to the weight of the catalyst usually being in the range 0.7% to 80% by weight, preferably in the range 1% to 50% by weight, and more preferably in the range 5% to 40% by weight.

In the case in which several zeolites are used, they may be incorporated into a single matrix or into several different matrixes. The quantity of zeolite with form selectivity in the total quantity is less than 30% by weight.

The catalyst used in the catalytic cracking reactor may be constituted by an ultra-stable Y type zeolite dispersed in a matrix of alumina, silica or silica-alumina, to which an additive based on ZSM-5 zeolite has been added, the quantity of ZSM-5 crystals in the total quantity being less than 30% by weight.

The unit for separating effluents from the reactor of the catalytic cracking unit (FCC) generally comprises a primary separation of the FCC effluents, a section for compression and fractionation of gases as well as distillations to fractionate the various liquid cuts. This type of fractionation unit is well known to the skilled person.

2) Oligomerization

The aim of this step is to oligomerize C2 to C9 olefins which may be formed from several disjointed cuts such as, for example, a C3 to C6 cut and a C8 to C9 cut, to obtain a mixture of hydrocarbons containing mono-olefins mainly containing 9 or more C atoms. Typically, from C4 olefins, oligomers are obtained with a number of carbon atoms that for the majority is 30 or less, and for the vast majority is in the range 8 to 20.

Oligomerization can be distinguished from polymerization by the addition of a limited number of molecules. In the context of the invention, the number of molecules which are added is in the range 2 to 10, limits included, and generally in the range 2 to 5, in particular in the range 2 to 4.

The oligomerates may, however, comprise traces of olefins that have been oligomerized containing more than 10 molecules. Usually, these traces represent less than 5% by weight with respect to the oligomers formed.

The oligomerization may be carried out in one or more steps, with one or more reactors arranged in parallel or in series, and one or more catalysts. The following description of the catalyst and the operating conditions may be applied to any one of the steps and/or to any one of the reactors.

The oligomerization catalyst used is preferably a catalyst based on silica-alumina or zeolite. The operating temperature is in the range 100° C. to 350° C., preferably in the range 150° C. to 270° C. The operating pressure is in the range 1 to 10 MPa (1 MPa=$10^6$ Pascal=10 bar).

The invention will now be explained in more detail with the aid of the description of the FIGURE representing the layout of the process of the invention.

The feed 1 is introduced into the FCC unit 2 along with an alternative feed 17 with an initial boiling point of 220° C., preferably 150° C., which can represent up to 30% of the FCC feed, preferably less than 20%. This feed 17 is optional as the process of the invention can operate perfectly well with the single feed 1.

Conventionally, the following are extracted from the FCC unit 2, in increasing molecular weight order:

a dry gas cut 3 constituted by hydrogen, $H_2$, methane and possibly ethane, ethylene and propane;

a cut 7 formed by C2 to C9 molecules the treatment of which forms the subject matter of the present invention;

a gasoline cut 16 with a distillation range in the range 25° C. to 150° C. or even up to 220° C.;

a cut 4 termed a "distillate", usually denoted LCO (light cycle oil);

a "slurry" cut 5 which is added to the fuel pool.

In certain cases, the cut 7 may be sent to a series of units 8 (generally selective hydrogenation units to remove the diolefins or nitrogen-containing compounds) which produce the feed 11 supplied to the oligomerization unit 12.

Additional olefinic cuts 9 originating from other units may be added to the stream 7 or to the stream 11 depending on the necessity or otherwise for them to undergo a hydrotreatment in the units 8.

Three cuts are extracted from the oligomerization unit 12:

a cut 13 termed a raffinate which corresponds to unconverted olefins and to the paraffins in the feed 11, which may be directed to the gasoline pool;

a cut termed a light oligomerate 15 with an end point which is less than 150° C., preferably less than 170° C. This cut constitutes the specific recycle for the FCC unit;

a cut 14 termed the heavy oligomerate which has a boiling point of more than 130° C. and preferably more than 150° C., and which is incorporated into the middle distillate 4.

EXAMPLES

Three examples will now be provided to illustrate the improved performance of the process of the present invention (Examples 2 and 3) compared with the prior art process (Example 1).

Example 1 (Prior Art): Reference Case

This first example constitutes the basic case and corresponds to a FCC unit with a single riser with a capacity of 40000 BPSD, i.e. 265 m³/hour (BPSD is the abbreviation for barrels per day), treating a mixture of 70% of hydrotreated VGO and 30% of straight run VGO (i.e. directly from a vacuum distillation unit). The FCC unit functions with a catalytic system constituted by silica-alumina.

The principal characteristics of the feed and the operating conditions employed are respectively presented in Tables 1 and 2 below:

TABLE 1

| Principal characteristics of VGO feed | | |
|---|---|---|
| Density 15/4° C. | | 0.91 |
| Sulphur | Weight % | 0.65 |
| Nitrogen | ppm by weight | 900 |
| Conradson carbon | Weight % | <0.1 |
| Nickel | ppm by weight | <0.1 |
| Vanadium | ppm by weight | <0.1 |
| Hydrogen | Weight % | 12.7 |

TABLE 2

Operating conditions of FCC, Example 1

|  |  | Example 1 |
|---|---|---|
| Capacity of FCC unit, VGO feed | Barrel/day | 40000 |
| Flow rate of VGO feed | t/h | 241 |
| Pressure, riser outlet | Bar g | 1.4 |
| Temperature, riser outlet | ° C. | 500 |
| Temperature of feed preheat | ° C. | 280 |
| Vapour flow rate | t/h | 16.8 |
| Ratio of mass flow rate of catalyst over flow |  | 6.4 |

Under these conditions, the yields with respect to the feed for the unit outlet products are given in Table 3:

TABLE 3

Yields of products from Example 1

| Weight % | basic case |
|---|---|
| Dry gases | 1.80 |
| LPG | 16.15 |
| C3 | 1.34 |
| C3 = | 4.79 |
| C4 total | 10.11 |
| Gasoline (IP-150° C.) | 39.14 |
| LCO (150-370° C.) | 30.35 |
| Slurry (370° C.+) | 7.66 |
| Coke | 4.81 |
| Total | 100 |

Example 2: Concatenation of a FCC Unit with a Unit for Oligomerizing C4 to C6 Olefins with No Recycle of Light Oligomerate In Example 2, the FCC unit functions under the same conditions as those described for Example 1, but this time the C4 and C5-C6 cuts are sent to an oligomerization unit functioning on a zeolitic catalyst under the operating conditions shown in Table 4 with no recycle of light oligomerate.

TABLE 4

Operating conditions of oligomerization unit, Example 2

| Oligomerization unit |  |  |
|---|---|---|
| Flow rate of C4, C5 and C6 feed | t/h | 115 |
| Temperature | ° C. | 250 |
| Pressure | Bar g | 15 |

Under these conditions, the product yields with respect to the heavy feed for the FCC unit are given in Table 5:

TABLE 5

Flow rates of products from Example 2

| Weight % | FCC + oligomerization with no recycle of light oligomerate |
|---|---|
| Dry gases | 1.86 |
| LPG | 11.46 |
| C3 | 1.34 |
| C3 = | 4.78 |
| C4 total | 5.34 |
| Gasoline (IP-150° C.) | 33.17 |
| LCO (150-370° C.) | 41.06 |

TABLE 5-continued

Flow rates of products from Example 2

| Weight % | FCC + oligomerization with no recycle of light oligomerate |
|---|---|
| Slurry (370° C.+) | 7.65 |
| Coke | 4.8 |
| Total | 100 |

The concatenation of a FCC unit with an oligomerization unit, operated under operating conditions which can orientate the performance towards the middle distillate, significantly improves the overall production of LCO.

In the basic case, this LCO production represents 30.3% by weight of the FCC feed, as opposed to 41.1% by weight in the novel configuration of the present invention, i.e. an increase of 36%.

The gasoline cut reduces by 15%, changing from 39.1% by weight in the basic case to 33.2% by weight.

The selectivity for LCO compared with gasoline (LCO/gasoline ratio) was thus improved, changing from 0.77 to 1.24, which is a considerable improvement in regard to the changing scenarios in the fuel market.

Example 3 (in Accordance with the Invention): Concatenation of a FCC Unit with a Unit for Oligomerizing C4 to C6 Olefins with a Recycle of Light Oligomerate Example 3 is a repeat of Example 2, but with a recycle of the light oligomerate to the FCC riser upstream of the feed. This recycle affected the coke yield, and so the thermal balance of the FCC was affected and thus its operating conditions were also affected. The operating conditions are presented in Table 6:

TABLE 6

Operating conditions for FCC, Example 3

| Capacity of FCC unit, VGO feed | Barrel/day | 40000 |
|---|---|---|
| Flow rate of VGO feed | t/h | 241 |
| Recycle flow rate for light oligomerate | t/h | 21.7 |
| Pressure, riser outlet | Bar g | 1.4 |
| Temperature, riser outlet | ° C. | 500 |
| Temperature of heavy feed preheat | ° C. | 280 |
| Vapour flow rate | t/h | 16.8 |
| Ratio of mass flow rate of catalyst over flow rate of feed |  | 6.9 |

Under these conditions, the product yields with respect to the heavy feed for the FCC changed, as can be seen in Table 7:

TABLE 7

Flow rates of products from Example 3

| Weight % | FCC + oligomerization with recycle of light oligomerate |
|---|---|
| Dry gases | 2.46 |
| LPG | 14.06 |
| C3 | 1.59 |
| C3 = | 7.13 |
| C4 total | 5.34 |
| Gasoline (IP-150° C.) | 27.57 |
| LCO (150-370° C.) | 43.09 |

TABLE 7-continued

Flow rates of products from Example 3

| Weight % | FCC + oligomerization with recycle of light oligomerate |
|---|---|
| Slurry (370° C.+) | 7.61 |
| Coke | 5.21 |
| Total | 100 |

Recycling the light oligomerate meant that 2 supplemental percentage points were gained for the LCO, causing the yield for this cut to change from 41.1% to 43.1% by weight. It also significantly reduced the production of gasoline by 5.6 points. The selectivity for LCO compared with gasoline was thus improved, changing from 1.24 to 1.56.

Compared with Example 2 of the prior art, associating a FCC unit and an oligomerization unit with a recycle of the light oligomerate 15 meant that 12.7 points were gained for the LCO, the gasoline fraction was reduced by 11.6 points and the LCO selectivity was very significantly improved compared with gasoline (1.56 as opposed to 1.24).

The invention claimed is:

1. A process for the conversion of a heavy hydrocarbon feed with an initial boiling point of 340° C. or more into a middle distillate having a distillation range of from 130° C. to 410° C., said process comprising:
   catalytically cracking the heavy hydrocarbon feed in a catalytic cracking unit (2) to obtain a wide cut (7) containing 2 to 9 carbon atoms and the middle distillate;
   optionally hydrotreating the wide cut (7) in a hydrotreatment unit (8);
   oligomerizing the optionally hydrotreated wide cut (7) in an oligomerization unit (12) under operating conditions of a temperature in the range of 100° C. to 350° C. and a pressure in the range 1 to 10 MPa to obtain an effluent;
   separating the effluent from the oligomerization unit (12) into three cuts:
      a raffinate cut (13) comprising unconverted olefins and paraffins of the feed (7);
      a light oligomerate cut (15) with a boiling point of less than 180° C.;
      a heavy oligomerate cut (14) with a boiling point of more than 130° C.;
   recycling the light oligomerate cut (15) as a secondary feed to the catalytic cracking unit (2) for catalytic cracking; and
   adding the heavy oligomerate cut (14) to the middle distillate produced by the catalytic cracking.

2. The process of claim 1, wherein a cut (17) which comprises C2 to C9 olefins is added to the catalytic cracking unit (2) either by mixing the cut (17) with the light oligomerate cut (15) before the light oligomerate cut (15) is recycled or by adding the cut (17) directly to the catalytic cracking unit (2).

3. The process of claim 2, wherein the cut (17) which comprises C2 to C9 olefins is formed from a C3 to C6 cut and a C8 to C9 cut, wherein each of the C3 to C6 cut and the C8 to C9 cut is derived from a process selected from the group consisting of: a coking process, a visbreasking process, an alcohol to olefins conversion process, a steam cracking process, and a Fischer-Tropsch synthesis process.

4. The process of claim 1, wherein the catalytic cracking unit (2) comprises a single riser in an upward flow mode and is operated at a reactor outlet temperature in the range of 450° C. to 650° C. and a C/O ratio in the range of 2 to 20.

5. The process of claim 1, wherein the catalytic cracking unit (2) comprises a single riser in an upward flow mode and is operated at a reactor outlet temperature in the range of 470° C. to 620° C. and a C/O ratio in the range of 4 to 15.

6. The process of claim 1, wherein the catalytic cracking unit (2) comprises two distinct riser reactors, wherein:
   one riser reactor treats the heavy hydrocarbon feed under the following conditions: a reactor outlet temperature in the range of 450° C. to 640° C. and a C/O ratio in the range of 2 to 20; and
   the other riser reactor treats the recycled light oligomerate cut under the following conditions: a reactor outlet temperature in the range of 500° C. to 750° C. and a C/O ratio in the range of 8 to 40.

7. The process of claim 1, wherein the catalytic cracking unit (2) comprises two distinct riser reactors, wherein:
   one riser reactor treats the heavy hydrocarbon feed under the following conditions: a reactor outlet temperature in the range of 470° C. to 620° C. and a C/O ratio in the range of 4 to 15; and
   the other riser reactor treats the recycled light oligomerate cut under the following conditions: a reactor outlet temperature in the range of 570° C. to 650° C. and a C/O ratio in the range of 8 to 40.

8. The process of claim 1, wherein the catalytic cracking unit (2) comprises a catalyst and the catalyst comprises a zeolite with form selectivity selected from the group consisting of: MEL, MFI, NES, EUO, FER, CHA, MFS and MWW.

9. The process of claim 8, wherein the zeolite with said form selectivity is selected from the group consisting of: ZSM-11, ZSM-5 and SAPO-34.

10. The process of claim 8, wherein the proportion of zeolite with said form selectivity, with respect to the weight of the catalyst, is in the range of 5% to 40%.

11. The process of claim 1, wherein the catalytic cracking unit (2) comprises a catalyst and the catalyst comprises a zeolite with form selectivity selected from the group consisting of: NU-85, NU-86, NU-88 and IM-5.

12. The process of claim 1, wherein:
   the middle distillate has a distillation range of from 150° C. to 390° C.;
   the oligomerization unit (12) operates at a temperature in the range from 150° C. to 270° C.;
   the light oligomerate cut (15) has a boiling point of less than 150° C.; and
   the heavy oligomerate cut (14) has a boiling point of more than 150° C.

* * * * *